United States Patent [19]

Kolts et al.

[11] Patent Number: 4,658,077

[45] Date of Patent: Apr. 14, 1987

[54] COMPOSITION OF MATTER AND METHOD OF OXIDATIVE CONVERSION OF ORGANIC COMPOUNDS THEREWITH

[75] Inventors: John H. Kolts, Ochelata; James B. Kimble, Bartlesville, both of Okla.

[73] Assignee: Phillips Petroleum Company, Bartlesville, Okla.

[21] Appl. No.: 742,340

[22] Filed: Jun. 7, 1985

[51] Int. Cl.$^4$ .............................................. C07C 2/00
[52] U.S. Cl. ................................ 585/500; 585/415; 585/417; 585/418; 585/541; 585/654; 585/656; 585/657; 585/658; 585/661; 585/700; 585/943
[58] Field of Search ............... 585/415, 417, 418, 500, 585/541, 654, 656, 657, 658, 661, 702, 943

[56] References Cited

U.S. PATENT DOCUMENTS

| | | | |
|---|---|---|---|
| 1,863,212 | 6/1932 | Winkler | 585/415 |
| 3,810,953 | 5/1974 | Cichcwski | 585/658 |
| 3,845,156 | 10/1974 | Farha | 585/658 |
| 4,239,658 | 12/1980 | Mitchell, III et al. | 585/943 |
| 4,368,346 | 1/1983 | Eastman | 585/658 |
| 4,450,310 | 5/1984 | Fix et al. | 585/500 |
| 4,465,893 | 8/1984 | Olah | 585/943 |
| 4,497,970 | 2/1985 | Young | 585/417 |
| 4,523,049 | 6/1985 | Jones et al. | 585/500 |
| 4,523,050 | 6/1985 | Jones et al. | 585/415 |

OTHER PUBLICATIONS

Keller and Bhasen, "Synthesis of Ethylene via Oxidative Coupling of Methane," J. of Catalysis, 73, 9–19, (1982).
Hirsen and Baerns, "Oxidative Kippling via Methan ZuC$_2$-Kc Wen wassenrstuffen in Gegenwart Unter-Schieldlicher Katalysatcren", Chemical Zeitung, vol. 107, No. 7 & 8, 1983.
Fang and Yeh, "Catalytic Pyrolysis of Methane," J. Chinese Chemical Society, 29, 265–273, (1981).

Primary Examiner—William R. Dixon, Jr.
Assistant Examiner—Cynthia A. Prezluck
Attorney, Agent, or Firm—C. F. Steininger

[57] ABSTRACT

A solid composition of matter is disclosed consisting essentially of sodium, potassium, a Group IA metal or a Group IA metal and a Group IIA metal, titanium, oxygen and, optionally, at least one of a halogen and tin, in which at least one of the sodium, the potassium, the Group IA metal or the Group IIA metal is present in an amount in excess of any amount present in electrically neutral compounds of the metal, the titanium and oxygen.

The above compositions are particularly useful as solid contact materials for the oxidative conversion of feed organic compounds to product organic compounds, particularly in the presence of a free oxygen containing gas. A method for such conversion is also disclosed.

In a preferred embodiment a method for the oxidative conversion of methane, such as natural gas, to higher hydrocarbons, particularly ethylene and ethane, is disclosed in which the methane and a free oxygen containing gas are contacted with a Group IA metal, a Group IIA metal, or a Groun IA metal and a Group IIA metal, titanium, oxygen and, optionally, a halogen and/or tin.

26 Claims, No Drawings

COMPOSITION OF MATTER AND METHOD OF OXIDATIVE CONVERSION OF ORGANIC COMPOUNDS THEREWITH

The present invention relates to an improved composition of matter. In a more specific aspect, the present invention relates to a solid contact material adapted to oxidatively convert feed organic compounds to product organic compounds, particularly in the presence of a free oxygen containing gas, and a method for such conversion, particularly the conversion of methane to higher hydrocarbons.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-desorption process either of atomic or molecular oxygen and either on the surface or occluded within the solid material, oxidation-reduction utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen containing contact material, and, thereafter, reactivating or regenerating the contact material by again passing a free oxygen containing gas thereover. Such processes, thus, often require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock, since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectivity to ethylene are still quite low. Of particular interest in this phase of the art, is the oxidative conversion of methane to higher hydrocarbons, particularly ethylene and ethane and, more particularly, ethylene. However, these processes have, heretofore, resulted in low conversions of methane and poor selectivity to ethylene and ethane.

SUMMARY OF THE INVENTION

It is therefore an object of the present invention to provide an improved composition of matter and method of utilizing the same which overcomes the above and other disadvantages of the prior art. Another object of the present is to provide an improved composition of matter. Still another object of the present invention is to provide an improved contact material for the oxidative conversion of organic compounds to other organic compounds, particularly in the presence of a free oxygen containing gas. Another and further object of the present invention is to provide an improved method for the oxidative conversion of organic compounds to other organic compounds, particularly in the presence of a free oxygen containing gas. Another and further object of the present invention is to provide an improved method for the oxidative conversion of alkane hydrocarbons to other hydrocarbons, particularly in the presence of a free oxygen containing gas. A further object of the present invention is to provide a method for the oxidative conversion of organic compounds to other organic compounds, which results in improved conversion of feedstock. Yet another object of the present invention is to provide a method for the oxidative conversion of organic compounds to other organic compounds, which results in improved selectivity to desired products. A further object of the present invention is to provide a method for the oxidative conversion of organic compounds to other organic compounds, which results in improved conversion of feedstock and improved selectivity to desired products. Another and further object of the present invention is to provide a method for the oxidative conversion of organic compounds to other organic compounds, which utilizes temperatures below those of known processes. A still further object of the present invention is to provide a method for the oxidative conversion of organic compounds to other organic compounds, which reduces the energy requirements thereof. Another object of the present invention is to provide a method for the oxidative conversion of organic compounds to other organic compounds, which can be carried out in a continuous manner. Yet another object of the present invention is to provide a method for the oxidative conversion of organic compounds to other organic compounds, which extends the useful life of the contact material utilized. These and other objects of the present invention will be apparent from the following description.

The present invention includes a novel composition of matter selected from the group consisting of:

(a) a composition consisting essentially of: (1) at least one Group IA metal selected from the group consisting of sodium and potassium, (2) titanium, (3) oxygen and, optionally, (4) at least one material selected the group consisting of halogen ions, compounds containing halogen ions, tin and compounds containing tin, said at least one Group IA metal being present in an amount in excess of any amount present in electrically neutral compounds of said at least one Group 1A metal, said titanium and oxygen;

(b) a composition consisting essentially of: (1) at least one Group IIA metal, (2) titanium, (3) oxygen and, optionally, (4) at least one material selected from the group consisting of halogen ions, compounds containing halogen ions, tin and compounds containing tin, said at least one Group IIA metal being present in an amount in excess of any amount present in electrically neutral compounds of said at least one Group IIA metal, said titanium and oxygen; and (c) a composition consisting essentially of at least one Group IA metal, (2) at least one Group IIA metal, (3) titanium, (4) oxygen and, optionally, (5) at least one material selected from the group consisting of halogen ions, compounds containing halogen ions, tin and compounds containing tin, at least one of said at least one Group IA metal and said at least one Group IIA metal being present in an amount in excess of any amount present in electrically neutral compounds of said at least one of said Group IA metal, said titanium and oxygen and said at least one Group IIA metal, said titanium and oxygen.

In still another aspect, the present invention relates to a solid contact material, of one of the above compositions, adapted to convert feed organic compounds to product organic compounds, particularly in the presence of a free oxygen containing gas.

The present invention further provides an improved method for the conversion of feed organic compounds to product organic compounds, comprising:

contacting said feed organic compounds with a solid contact material selected from the group consisting of:

(a) a solid contact material consisting essentially of: (1) at least one Group IA metal selected from the group consisting of sodium and potassium, (2) titanium, (3) oxygen and, optionally, (4) at least one material selected from the group consisting of halogen ions, compounds containing halogen ions, tin and compounds containing tin, said at least one Group IA metal being present in an amount in excess of any amount present in electrically neutral compounds of said at least one Group IA metal, said titanium and oxygen;

(b) a composition consisting essentially of: (1) at least one Group IIA metal, (2) titanium, (3) oxygen and, optionally, (4) at least one material selected from the group consisting of halogen ions, compounds containing halogen ions, tin and compounds containing tin; said at least one Group IIA metal being present in an amount in excess of any amount present in electrically neutral compounds of said at least one Group IIA metal, said titanium and oxygen; and (c) a composition consisting essentially of: (1) at least one Group IA metal, (2) at least one Group IIA metal, (3) titanium, (4) oxygen and, optionally, (5) at least one material selected from the group consisting of halogen ions, compounds containing halogen ions, tin and compounds containing tin, at least one of said at least one Group IA metal and said at least Group IIA metal being present in an amount in excess of any amount present in electrically neutral compounds of said at least one Group IA metal, said titanium and oxygen and said at least one Group IIA metal, said titanium and oxygen, under oxidative conversion conditions sufficient to convert said feed organic compounds to said product organic compounds.

A still further aspect of the present invention provides an improved method for the conversion of methane to higher hydrocarbons, comprising:

contacting a feed material comprising methane and a free oxygen containing gas with a solid contact material selected from the group consisting of:

(a) a contact material comprising: (1) at least one Group IA metal, (2) titanium, (3) oxygen and, optionally, (4) a material selected from the group consisting of halogen ions, compounds containing halogen ions, tin and compound containing tin;

(b) a contact material comprising: (1) at least one Group IIA metal, (2) titanium, (3) oxygen and, optionally, (4) at least one material selected from the group consisting of halogen ions, compounds containing halogen ions, tin and compounds containing tin; and (c) a contact material comprising: (1) at least one Group IA metal, (2) at least one Group IIA metal, (3) titanium, (4) oxygen and, optionally, (5) at least one material selected from the group consisting of halogen ions, compounds containing halogen ions, tin and compounds containing tin, under oxidative conversion conditions sufficient to convert said methane to said higher hydrocarbons.

DESCRIPTION OF THE PREFERRED EMBODIMENTS

The improved composition of matter, of the present invention, is a composition of matter selected from the group consisting of:

(a) a composition consisting essentially of: (1) at least one Group IA metal selected from the group consisting of sodium and potassium, (2) titanium, (3) oxygen and, optionally, (4) at least one material selected from the group consisting of halogen ions, compounds containing halogen ions, tin and compounds containing tin, said at least one Group IA metal being present in an amount in excess of any amount present in electrically neutral compounds of said at least one Group IA metal, said titanium and oxygen;

(b) a composition consisting essentially of: (1) at least one Group IIA metal, (2) titanium, (3) oxygen and, optionally, (4) at least one material selected from the group consisting of halogen ions, compounds containing halogen ions, tin, and compounds containing tin, said at least one Group IIA metal being present in an amount in excess of any amount present in electrically neutral compounds of said at least one Group IIA metal, said titanium and oxygen; and (c) a composition consisting essentially of: (1) at least one Group IA metal, (2) at least one Group IIA metal, (3) titanium, (4) oxygen and, optionally, (5) at least one material selected from the group consisting of halogen ions, compounds containing halogen ions, tin, and compounds containing tin, at least one of said at least one Group IA metal and said at least one Group IIA metal being present in an amount in excess of any amount present in electrically neutral compounds of said at least one Group IA metal said titanium and oxygen and said at least one Group IIA metal, said titanium and oxygen.

Compositions, as set forth above, are useful as solid contact materials adapted to convert feed organic compounds to product organic compounds, particularly in the presence of a free oxygen containing gas.

The present invention further provides an improved method for the conversion of methane to higher hydrocarbons comprising:

contacting said methane and a free oxygen containing gas with a solid contact material selected from the group consisting of:

(a) a contact material comprising: (1) at least one Group IA metal, (2) titanium, (3) oxygen and, optionally, (4) a material selected from the group consisting of halogen ions, compounds containing halogen ions, tin and compounds containing tin;

(b) a contact material comprising: (1) at least one Group IIA metal, (2) titanium, (3) oxygen and, optionally, (4) at least one material selected from the group consisting of halogen ions, compounds containing halogen ions, tin and compounds containing tin; and (c) a contact material comprising: (1) at least one Group IA metal, (2) at least one Group IIA metal, (3) titanium, (4) oxygen and, optionally, (5) at least one material selected from the group consisting of halogen ions, compounds containing halogen ions, tin and compounds containing tin, under oxidative conversion conditions sufficient to convert said methane to said higher hydrocarbons.

The Group IA metals are preferably selected from the group consisting of lithium, sodium and potassium.

The Group IIA metals are preferably selected from the group consisting of magnesium, calcium, strotium and barium.

The halogen component is preferably chlorine.

When the term "effective amount" is utilized with reference to the composition of matter or contact materials herein, this term is meant to include more than an insignificant amount and, thus, a small amount sufficient to affect the function of the composition of matter and contact material for the purpose for which it is to be utilized.

The form in which the specified elements are present are the compositions of matter and contact materials of the present invention is not known. Possible compounds of the compositions of matter in the contact materials include oxides of titanium or mixtures thereof in the high or low valence state, sodium, potassium or Group IA metal titanates and mixtures thereof, either in high or low valence state, Group II metal titanates and mixtures thereof, in either the high or low valence state, or combinations of sodium, potassium or Group IA metal oxides in combination with sodium, potassium, Group IA, or Group IIA titanates and mixtures thereof, either in the high or low valence state. Accordingly, it is to be understood that the present invention is not to be limited to any particular theory of the form of the compositions of matter and the contact materials or the manner in which these compositions of matter and contact materials function in the methods of the present invention. However, it has been found, in accordance with the present invention, that the compositions of matter and contact materials do contain what may be termed "free" sodium, potassium, Group IA metals and Group IIA metals in addition to or in excess of any amount of sodium, potassium, Group IA metal and/or Group IIA metal which may be present in electrically neutral compounds of the Group IA metal, the titanium and oxygen or electrically neutral compounds of the Group IIA metal, the titanium and oxygen. The free or excess sodium, potassium, Group IA metal and/or Group IIA metal is believed to be in the form of oxides or carbonates of said metal. For example, the excess sodium, potassium, Group IA metal and/or Group IIA metal may be incorporated in the composition of matter or contact material as a carbonate or it may initially be in the form of an oxide, which it is believed is converted to a carbonate during the course of the methods of the present invention, in the presence of a free oxygen containing gas. Similarly the excess sodium, potassium, Group IA metal and/or Group IIA metal may be initially in the form of carbonates and be converted to oxides during the course of the hereinafter mentioned drying in the presence of a free oxygen containing gas or calcination in the presence of a free oxygen containing gas. For example, it is believed that in the combinations containing sodium, potassium or Group IA metals, titanium and oxygen, the materials first form electrically neutral sodium, potassium or Group IA metal titanates ($Na_2Ti_3O_7$, $K_2TiO_3$, etc.) and, as additional sodium, potassium or Group IA metal is added, it appears as free or excess metal in the form of an oxide or carbonate. Similarly, Group IIA metals are believed to first form electrically neutral Group IIA metal titanates and, as additional Group IIA metals are added, they are present as free or excess Group IIA metal, probably in the form of oxides or carbonates. In the combinations of sodium, potassium or Group IA metals, Group IIA metals, titanium and oxygen, it is believed that the Group IIA metals are present in the form of electrically neutral Group IIA metal titanates and the sodium, potassium or Group IA metal is present as free or excess metal, probably in the form of oxides or carbonates. Consequently, when the phrase "consisting essentially of" is utilized in the specification and claims hereof, this phrase is meant to include the oxides, carbonates or other compounds in which the free or excess potassium, sodium, Group IA metal and/or Group IIA metal may be present. It is also to be understood that when the phrases, "an amount in excess of any amount present in electrically neutral compounds of the titanium and oxygen" or "electrically neutral compounds of Group IIA metal, the titanium and oxygen" are utilized, this terminology is meant to include effective amounts of free or excess sodium, potassium, Group IA metal and/or Group IIA metal when the titanium is in the form of titanium oxides, sodium, potassium or Group IA titanates or Group IIA metal titanates. Accordingly, the above compositions of matter and contact materials contain from an effective amount of free or excess sodium, potassium, Group IA metal, or Group IIA metal to near 100%, so long as an effective amount of electrically neutral compounds of the titanium and oxygen, such as titanium oxides, sodium, potassium or Group IA metal titanates and/or Group IIA metal titanates are present. It has been found, in accordance with the present invention, that both the free or excess metal, as defined, and the electrically neutral compounds of the titanium are necessary to perform the function of contact materials, in accordance with the present invention. Usually, the free or excess sodium, potassium, or the Group IA metal will be present in amounts from about 0.1 wt. % to about 50 wt. % (depending upon the atomic weight of the element), expressed in terms of elemental metal based on the total weight of the composition or contact material. Preferred ranges of free or excess sodium, potassium, or Group IA metals are between about 0.5 wt. % and about 15 wt. % and still more preferable amounts are between about 1 wt. % and about 5 wt. %. Due to the fact that the Group IIA metals generally have higher atomic weights than the Group IA metals and vary over a broader range, the excess Group IIA metal will usually be present in amounts from about 0.001 to about 65 wt. %, preferably from 0.005 to about 20 wt. % and still more preferably between about 0.5 wt. % and about 5 wt. %. Halogen, when present, is utilized in amounts from an effective amount to near 100 wt. %, usually between about 0.1 wt. % and about 5 wt. %, expressed as elemental chlorine based on the total weight of the composition or contact material. Where tin is utilized, it may be present from an effect amount to near 100 wt. %, usually between about 0.5 wt. % and 20 wt. % and preferably between about 1 wt. % and about 7 wt. % expressed in terms of elemental tin, based on the total weight of the composition of matter or contact material. Where both halogen and tin are present, a convenient form of these materials is as tin halide. It should again be emphasized that the amounts of the metals and halides, as indicated above, are expressed herein and in the claims in terms of the elemental metal or elemental halogen based on the total weight of the active components of the composition of matter or contact material.

The above-mentioned components of the novel composition of matter and compositions of matter and contact materials can be mixed with or deposited on an "inert support material" adapted to harden or support the active materials. The term "inert support material" when utilized in this context is meant to include any material which does not react with or exchange ions with the active components. Where such solid support material is utilized, the weight of such solid support material is not included in determining the relative weights of the active components.

The sodium, potassium, Group IA metal, Group IIA metal, titanium, or chloride or tin can be derived from any suitable source of such materials, such as carbonates, hydroxides, oxides, nitrates, octoates, halides, etc. The compositions of matter and contact materials can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. For example, a contact material containing 2% by wt. of free or excess lithium can be prepared by forming an aqueous slurry of 100 grams of titanium oxide ($TiO_2$) with 2 grams of elemental lithium, as 10.5 grams of lithium carbonate ($Li_2CO_3$). Alternatively, this same material can be prepared by impregnating 100 grams of titanium oxide with 2 grams of elemental lithium as 19.7 grams of lithium nitrate. A composition containing 3% free or excess lithium, magnesium, titanium and oxygen can be prepared by forming an aqueous slurry of 100 grams of magnesium titanate ($Mg_2TiO_4$) with 3% of elemental lithium, as 15.7 grams of lithium carbonate ($Li_2CO_3$), or by impregnating 100 grams of magnesium titanate with 30 grams of lithium nitrate. Irrespective of the starting materials or the method of combining the materials, the composition or contact material is dried, if in the form of an aqueous slurry or in a solvent, usually at a temperature sufficient to volatilize the water or other carrier, such as about 220° F. to about 450° F. in the presence of a free oxygen containing gas. Whether combined by slurrying, impregnation or other techniques, the thus combined materials are then calcined in the presence of a free oxygen containing gas, usually at temperatures between about 700° F. and about 1200° F. for from 1 to about 24 hours. Where halogen ions and/or tin are present, the previously prepared dried materials can be impregnated with appropriate compounds of halide or tin, such as a hexane solution of tin octoate or tin halide. The resultant composition is again dried and calcined. Calcining may be delayed until after impregnation with halide and/or tin.

These compositions of matter and contact materials are particularly useful for the oxidative conversion of feed organic compounds to product organic compounds, in the presence of a free oxygen containing gas. Processes of this character include the oxidative dehydrogenation of hydrocarbons, particularly alkanes having 2 to 7 carbon atoms, to other hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The compositions of matter and contact materials of the present invention are particularly useful for the oxidative conversion of methane to higher hydrocarbons, particularly the oxidative conversion of methane to ethylene, in the presence of a free oxygen containing gas.

The conditions of operation of such processes for the oxidative conversion of feed organic compounds to product organic compounds can vary over a wide range. Such conditions are either known to those skilled in the art or can be readily optimized by one skilled in the art by simple, conventional experiments.

Since the composition of matter and contact materials of the present invention are highly effective for the oxidative conversion of methane to higher hydrocarbons, particularly ethylene and ethane, and this process is of great value, the conversion of feed organic materials to product organic materials will be illustrated and exemplified by such methane conversion.

In accordance with most previous theories of the function and operation of contact materials for the oxidative conversion of methane to higher hydrocarbons, and particularly ethylene and ethane, the reaction has been carried out in the absence of a free oxygen containing gas, with the oxygen theoretically being supplied by the contact material. As a result, the most utilized modes of operation have included treating the contact material with a free oxygen containing gas, such as oxygen or air, for a period of time sufficient to produce a reducible oxide of a multivalent metal, thereafter, contacting methane with the reducible metal oxide and, thereafter, treating the metal oxide with a free oxygen containing gas to "regenerate" the same. Similarly, certain contact materials are contacted with a free oxygen containing gas to cause adsorption of oxygen on the contact material, methane is, thereafter, contacted with the contact material containing adsorbed oxygen and, thereafter, the contact material is again treated with a free oxygen containing gas. In both instances, the contact material, after treatment with a free oxygen containing gas, is usually purged with an inert gas, such as nitrogen, to remove excess oxygen which has not reacted with or been adsorbed on the contact material. Consequently, several techniques have been followed, including, carrying out the contact with methane and the contact with a free oxygen containing gas in separate reaction chambers or sequentially passing a free oxygen containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material, in the presence of a free oxygen containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are most often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent gas" is meant to include any gaseous material or material which is in vapor form during the reaction which is present in the methane-containing gas, the free oxygen containing gas or in the form of an added gas vapor which is essentially inert with respect to the oxidative conversion of methane and, thus, does not significantly decrease the conversion of methane and/or the selectivity to the production of higher hydrocarbons.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

The contact materials of the examples were prepared by aqueous slurrying, drying and calcination, as described previously. Where small amounts of Group IA metals were utilized (contact materials 2, 6, 7, 11, 12, 13, 15, 16, 17, 18 and 19) are present, the Group IA metal was added by impregnating the major component with a Group IA metal nitrate. In the examples of the Table, the starting materials were electrically neutral titanium oxide ($TiO_2$ or $TiO_4$) and electrically neutral Group IIA metal titanates ($Mg_2TiO_4$, $Ca_2TiO_4$ and $Sr_2TiO_4$). The atomic proportions of the Group IIA metal to titanium were measured from samples of the starting materials. An aqueous slurry was formed from these starting materials containing titanium and appropriate compounds of Group IA metals in appropriate amounts. The parenthetic percentages in the Table thus represent the weight percent of free or excess Group IA metal, as previously explained, expressed in terms of the elemental metal based on the total weight of the composition or contact material. The free or excess Group IA metal is believed to be in an oxide or carbonate form.

In the runs of the examples, the contact material was loaded in a quartz reactor having a thermocouple well centered in the contact material bed. The reactor was brought up to temperature under nitrogen or air and thereafter methane and air (or oxygen) flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography. All contact materials are referred to in terms of weight percent of the designated element, based on the total weight of contact material.

The variables and results of this series of tests are set forth in the Table below. Conversion is mole percent of methane converted. Selectivity is based on mole percent of methane feed converted to a particular product. The $CH_4$ rate can be expressed as cc/min/cc of contact material. For example, when 70 cc/min of $CH_4$ was fed to a reactor containing 20 cc of catalyst the flow rate would be 3.5 cc/min of $CH_4$/cc of contact material. The volumetric ratio of $CH_4$ to oxygen or other gas is also given in terms of cc/min of $CH_4$ per cc/min of other gases (air or $N_2$ etc.) present.

TABLE

| Run No. | Contact Material | Volume | Volume of Con. Mat. | Sample Time(min) | Temp (°C.) | Conversion | Selectivity % | | | | | | |
|---|---|---|---|---|---|---|---|---|---|---|---|---|---|
| | | | | | | | $C_2=$ | $C_2$ | $C_2$'s | $C_3=$ | $C_3$ | $CO_2$ | CO |
| | | $CH_4/O_2$ | | | | | | | | | | | |
| 1 | $TiO_2$ | 314/21 | 25 cc | 10 | 604.0 | 3.8 | 0.0 | 0.0 | 0.0 | 0.0 | 0.0 | 40.2 | 59.4 |
| | | | | 40 | 653.0 | 5.0 | 0.0 | 0.0 | 0.0 | 0.0 | 0.0 | 27.1 | 72.9 |
| | | | | 122 | 703.0 | 5.3 | 0.0 | 0.0 | 0.0 | 0.0 | 0.0 | 25.4 | 74.3 |
| | | | | 172 | 751.0 | 5.2 | 0.0 | 0.0 | 0.0 | 0.0 | 0.0 | 26.2 | 73.5 |
| | | | | 216 | 800.0 | 5.9 | 0.0 | 0.0 | 0.0 | 0.0 | 0.0 | 27.2 | 72.6 |
| | | $CH_4/Air$ | | | | | | | | | | | |
| 2 | Li(2%)/$TiO_2$ | 83/83 | 20 cc | 5 | 730.0 | 5.0 | 0.0 | 1.9 | 1.9 | 0.0 | 0.0 | 78.9 | 19.2 |
| | | | | 39 | 723.0 | 3.4 | 5.3 | 24.7 | 30.0 | 0.0 | 0.0 | 55.3 | 14.6 |
| | | | | 74 | 720.0 | 2.5 | 4.9 | 28.2 | 33.1 | 0.0 | 0.0 | 52.8 | 13.3 |

TABLE-continued

| Run No. | Contact Material | Volume | Volume of Con. Mat. | Sample Time(min) | Temp (°C.) | Conversion | Selectivity % | | | | | | |
|---|---|---|---|---|---|---|---|---|---|---|---|---|---|
| | | | | | | | $C_2=$ | $C_2$ | $C_2's$ | $C_3=$ | $C_3$ | $CO_2$ | CO |
| | | | | 109 | 723.0 | 2.0 | 3.6 | 28.8 | 32.4 | 0.0 | 0.0 | 53.6 | 14.4 |
| 3 | Li(5%)/TiO$_2$ | 313/104 | 25 cc | 5 | 671.0 | 0.6 | 0.0 | 25.9 | 25.9 | 0.0 | 0.0 | 24.5 | 47.1 |
| | | | | 44 | 700.0 | 0.9 | 0.0 | 32.5 | 32.5 | 0.0 | 0.0 | 22.1 | 43.3 |
| | | | | 87 | 725.0 | 1.6 | 6.2 | 34.3 | 40.5 | 0.0 | 0.0 | 20.3 | 38.0 |
| | | | | 120 | 752.0 | 2.6 | 9.7 | 35.4 | 45.1 | 0.0 | 0.0 | 20.0 | 34.9 |
| | | | | 149 | 799.0 | 5.3 | 18.3 | 30.5 | 48.8 | 0.0 | 0.0 | 20.4 | 30.8 |
| | | | | 189 | 700.0 | 0.6 | 0.0 | 26.4 | 26.4 | 0.0 | 0.0 | 28.8 | 44.8 |
| 4 | Li(10%)/TiO$_2$ | 313/104 | 25 cc | 5 | 650.0 | 0.1 | 0.0 | 100.0 | 100.0 | 0.0 | 0.0 | 0.0 | 0.0 |
| | | | | 41 | 700.0 | 0.4 | 0.0 | 91.4 | 91.4 | 0.0 | 0.0 | 8.6 | 0.0 |
| | | | | 81 | 750.0 | 1.4 | 16.9 | 69.8 | 86.7 | 0.0 | 0.0 | 4.6 | 8.7 |
| | | | | 115 | 775.0 | 1.9 | 21.5 | 64.9 | 86.4 | 0.0 | 0.0 | 4.6 | 9.0 |
| | | | | 149 | 800.0 | 2.4 | 26.8 | 59.3 | 86.1 | 0.0 | 0.0 | 4.6 | 9.3 |
| | | | | 183 | 701.0 | 0.1 | 0.0 | 100.0 | 100.0 | 0.0 | 0.0 | 0.0 | 0.0 |
| 5 | Li(31%)/TiO$_2$ | 313/104 | 25 cc | 10 | 502.0 | 0.0 | — | — | — | — | — | — | — |
| | | | | 55 | 554.0 | 0.1 | 0.0 | 100.0 | 100.0 | 0.0 | 0.0 | 0.0 | 0.0 |
| | | | | 65 | 601.0 | 0.2 | 0.0 | 66.9 | 66.9 | 0.0 | 0.0 | 33.1 | 0.0 |
| | | | | 106 | 650.0 | 1.1 | 6.3 | 70.2 | 76.5 | 0.0 | 0.0 | 23.5 | 0.0 |
| | | | | 147 | 700.0 | 4.1 | 14.3 | 58.2 | 72.5 | 0.0 | 0.0 | 25.9 | 1.7 |
| | | | | 182 | 750.0 | 8.0 | 23.5 | 43.9 | 67.4 | 1.4 | 0.0 | 30.4 | 0.8 |
| | | | | 244 | 800.0 | 11.0 | 37.2 | 31.5 | 68.7 | 3.9 | 0.0 | 24.5 | 1.2 |
| 6 | Na(3%)/TiO$_2$ | 104/104 | 25 cc | 10 | 702.0 | 13.0 | 1.9 | 5.4 | 7.3 | 0.0 | 0.0 | 77.0 | 15.7 |
| | | | | 46 | 702.0 | 13.1 | 2.4 | 6.3 | 8.7 | 0.0 | 0.0 | 75.9 | 15.5 |
| | | | | 80 | 702.0 | 13.1 | 2.4 | 6.5 | 8.9 | 0.0 | 0.0 | 75.8 | 15.3 |
| 7 | K(3%)/TiO$_2$ | 104/104 | 25 cc | 7 | 701.0 | 12.3 | 5.0 | 17.8 | 22.8 | 0.0 | 0.0 | 77.3 | 0.0 |
| | | | | 43 | 702.0 | 12.6 | 6.3 | 19.6 | 25.9 | 0.0 | 0.0 | 74.1 | 0.0 |
| | | | | 90 | 702.0 | 12.8 | 6.4 | 19.7 | 26.1 | 0.0 | 0.0 | 73.8 | 0.0 |
| | | | | 126 | 701.0 | 13.1 | 6.2 | 19.4 | 25.6 | 0.0 | 2.8 | 71.7 | 0.0 |
| 8 | Mg$_2$TiO$_4$ | 104/104 | 25 cc | 5 | 700.0 | 10.2 | 0.0 | 0.0 | 0.0 | 0.0 | 0.0 | 67.9 | 31.1 |
| | | | | 51 | 710.0 | 10.3 | 0.0 | 0.0 | 0.0 | 0.0 | 0.0 | 66.3 | 33.7 |
| | | | | 95 | 708.0 | 10.2 | 0.0 | 0.0 | 0.0 | 0.0 | 0.0 | 67.2 | 32.8 |
| 9 | Ca$_2$TiO$_4$ | 104/100 | 25 cc | 5 | 709.0 | 13.6 | 0.0 | 3.1 | 3.1 | 0.0 | 0.0 | 66.4 | 30.5 |
| | | | | 58 | 707.0 | 13.1 | 1.2 | 4.2 | 5.4 | 0.0 | 0.0 | 67.4 | 27.3 |
| | | | | 98 | 706.0 | 12.3 | 0.0 | 4.4 | 4.4 | 0.0 | 0.0 | 68.9 | 26.6 |
| | | | | 140 | 706.0 | 12.0 | 1.2 | 4.8 | 6.0 | 0.0 | 0.0 | 68.2 | 25.8 |
| 10 | Sr$_2$TiO$_4$ | 104/100 | 25 cc | 17 | 710.0 | 13.4 | 1.7 | 7.1 | 8.8 | 0.0 | 0.0 | 61.8 | 29.3 |
| | | | | 49 | 708.0 | 12.7 | 3.0 | 10.1 | 13.1 | 0.0 | 0.0 | 61.1 | 25.8 |
| | | | | 85 | 709.0 | 12.6 | 3.6 | 11.0 | 14.6 | 0.0 | 0.0 | 60.9 | 24.5 |
| | | | | 119 | 708.0 | 12.6 | 3.8 | 11.5 | 15.3 | 0.0 | 0.0 | 60.5 | 24.2 |
| 11 | Li(3%)/Mg$_2$TiO$_4$ | 100/100 | 24 cc | 9 | 708.0 | 2.6 | 14.7 | 54.4 | 69.1 | 0.0 | 0.0 | 16.3 | 14.6 |
| | | | | 44 | 707.0 | 2.5 | 13.9 | 55.0 | 68.9 | 0.0 | 0.0 | 16.2 | 14.9 |
| | | | | 96 | 708.0 | 2.4 | 13.7 | 56.2 | 69.9 | 0.0 | 0.0 | 15.6 | 14.5 |
| | | | | 136 | 708.0 | 2.4 | 13.9 | 56.1 | 70.0 | 0.0 | 0.0 | 15.8 | 14.2 |
| | | | | 168 | 753.0 | 7.3 | 32.2 | 43.2 | 75.4 | 0.0 | 0.0 | 11.7 | 12.9 |
| | | | | 203 | 754.0 | 7.4 | 32.8 | 42.7 | 75.5 | 0.0 | 0.0 | 11.3 | 13.1 |
| | | | | 204 | 751.0 | 8.2 | 33.5 | 38.8 | 72.3 | 2.8 | 0.0 | 12.0 | 13.0 |
| | | | | 257 | 800.0 | 19.3 | 40.4 | 17.5 | 57.9 | 5.0 | 0.0 | 12.3 | 18.1 |
| | | | | 300 | 800.0 | 19.3 | 39.9 | 17.5 | 57.4 | 5.0 | 0.0 | 11.9 | 17.7 |
| | | | | 349 | 800.0 | 18.8 | 41.9 | 18.0 | 59.9 | 5.1 | 0.0 | 12.6 | 18.9 |
| 12 | Li(3%)/Ca$_2$TiO$_4$ | 75/75 | 18 cc | 18 | 706.0 | 15.9 | 39.2 | 32.4 | 71.6 | 4.0 | 2.1 | 16.1 | 0.5 |
| | | | | 54 | 706.0 | 16.7 | 39.4 | 30.7 | 70.1 | 4.1 | 1.9 | 19.0 | 0.8 |
| | | | | 90 | 707.0 | 16.7 | 39.7 | 30.7 | 70.4 | 4.0 | 1.8 | 20.5 | 0.9 |
| | | | | 127 | 707.0 | 16.8 | 39.3 | 30.8 | 70.1 | 3.7 | 2.0 | 21.3 | 0.8 |
| | | | | 163 | 752.0 | 21.4 | 33.4 | 19.2 | 52.6 | 5.3 | 2.4 | 31.6 | 0.9 |
| 13 | Li(3%)/Sr$_2$TiO$_4$ | 61/61 | 14.5 cc | 10 | 708.0 | 13.0 | 43.4 | 44.7 | 88.1 | 4.6 | 3.5 | 1.3 | 0.0 |
| | | | | 46 | 705.0 | 13.7 | 42.2 | 43.2 | 85.4 | 4.4 | 3.4 | 0.9 | 0.0 |
| | | | | 88 | 708.0 | 14.6 | 42.6 | 42.1 | 84.7 | 4.1 | 3.4 | 0.9 | 0.0 |
| | | | | 126 | 710.0 | 14.7 | 43.7 | 44.3 | 88.0 | 4.5 | 3.8 | 1.0 | 0.0 |
| | | | | 161 | 706.0 | 13.1 | 41.9 | 49.1 | 91.0 | 3.8 | 3.5 | 1.7 | 0.0 |
| | | | | 207 | 710.0 | 15.4 | 31.1 | 34.3 | 65.4 | 2.8 | 1.5 | 26.9 | 1.5 |
| | | | | 242 | 710.0 | 15.4 | 31.5 | 34.8 | 66.3 | 2.7 | 1.6 | 27.0 | 1.5 |
| | | | | 287 | 709.0 | 15.9 | 32.1 | 33.5 | 65.6 | 2.9 | 0.0 | 29.9 | 1.3 |
| | | | | 330 | 749.0 | 21.0 | 36.5 | 21.7 | 58.2 | 3.7 | 0.9 | 31.5 | 1.2 |
| | | | | 383 | 750.0 | 20.7 | 38.6 | 22.3 | 60.9 | 4.1 | 1.2 | 27.3 | 1.2 |
| | | | | 442 | 676.0 | 9.4 | 27.5 | 48.9 | 76.4 | 0.0 | 0.0 | 22.2 | 1.4 |
| | | | | 482 | 654.0 | 5.9 | 20.0 | 56.1 | 76.1 | 0.0 | 0.0 | 22.0 | 1.9 |
| 14 | Zn$_2$TiO$_4$ | 70/80 | 20 cc | 40 | 717.0 | 11.0 | 2.0 | — | 2.0 | — | — | 91.0 | 7.0 |
| 15 | Li(3%)/Silica | 70/80 | 20 cc | 40 | 721.0 | 2.0 | 11.0 | — | 11.0 | — | — | 27.0 | 62.0 |
| 16 | Li(3%)/CaSilicate | 70/80 | 20 cc | 40 | 717.0 | 3.0 | — | — | — | — | — | 48.0 | 52.0 |
| 17 | Li(2%)/Al$_2$O$_3$ | 70/80 CH$_4$/N$_2$ | 20 cc | 40 | 700.0 | 15.0 | — | 3.0 | 3.0 | — | — | 64.0 | 33.0 |
| 18 | Li(3%)/Ca$_2$TiO$_4$ | 70/80 | 18 cc | 40 | 702.0 | 3.51 | — | 2.56 | 2.56 | — | — | 95.36 | 2.08 |
| | | | | 80 | 700.0 | 3.05 | — | 2.65 | 2.65 | — | — | 97.35 | — |
| | | | | 120 | 700.0 | 2.89 | — | — | — | — | — | 100.00 | — |
| 19 | Li(3%)/Sr$_2$TiO$_4$ | 70/80 | 14.5 cc | 40 | 700.0 | 1.41 | — | — | — | — | — | 87.08 | 17.93 |
| | | | | 80 | 701.0 | 0.95 | — | — | — | — | — | 83.17 | 16.23 |
| | | | | 120 | 701.0 | 0.79 | — | — | — | — | — | 85.10 | 14.90 |

Several significant observations are to be made from the data set forth in the Table. It is to be observed from Runs 2 through 5 that, as the amount of free or excess lithium approached electrically neutral lithium titanate ($Li_2TiO_3$-14 wt. percent elemental lithium), the selectivity to $C_2$ hydrocarbons, particularly ethylene, significantly increased and when the free or excess lithium was above electrically neutral lithium titanate (Run 5—31%) both conversion and selectivity improved once the contact material had become conditioned in the reaction. While the free or excess sodium and potassium in Runs 6 and 7 were below the amounts which would be present in electrically neutral sodium titanate and potassium titanate, respectively, it is to be observed that both conversion and selectivity were substantially better than equivalent amounts of free or excess lithium. Runs 8 through 10 illustrate that electrically neutral Group IIA titanates resulted in relatively high conversions but poor selectivity. However, the previous runs with free or excess Group IA metals, as well as parallel work, show that the free or excess Group IIA metals, probably in the oxide or carbonate form, in combination with the Group IIA metal titanates, will significantly improve the selectivity. Runs 11 through 13, utilizing the combination of a Group IA metal, a Group IIA metal, titanium and oxygen, are dramatically superior to any of the previous combinations, both in conversion of methane and selectivity to $C_2$ hydrocarbons, particularly ethylene. Runs 18 through 23 illustrate that, when no free oxygen is present, combinations of free or excess Group IA metal, Group IIA metals, titanium and oxygen produce poor conversions of methane and little or no selectivity to higher hydrocarbons.

It has also been found that the production of $CO_2$ was high and, hence, the HC selectivity was low, if the concentration of $O_2$ in the initial feed stream is high. Accordingly, the HC selectivity can be increased and the $CO_2$ production concomitantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

That which is claimed is:

1. A method for the oxidative conversion of methane to higher hydrocarbons, comprising:
   contacting a feed material comprising methane and a free oxygen-containing gas with a solid contact material selected from the group consisting of:
   (a) a contact material consisting essentially of: (1) at least one Group IA metal, (2) titanium and (3) oxygen;
   (b) a contact material consisting essentially of: (1) at least one Group IIA metal, (2) titanium and (3) oxygen;
   (c) a contact material consisting essentially of: (1) at least one Group IA metal, (2) at least one Group IIA metal, (3) titanium and (4) oxygen;
   (d) a contact material consisting essentially of: (1) at least one Group IA metal, (2) titanium, (3) oxygen and (4) at least one material selected from the group consisting of halogen ions and compounds containing halogen ions;
   (e) a contact material consisting essentially of: (1) at least one Group IIA metal, (2) titanium, (3) oxygen and (4) at least one material selected from the group consisting of halogen ions and compounds containing halogen ions; and
   (f) a contact material consisting essentially of: (1) at least one Group IA metal, (2) at least one Group IIA metal, (3) titanium, (4) oxygen and (5) at least one material selected from the group consisting of halogen ions and compounds containing halogen ions,
   under oxidative conversion conditions sufficient to convert said methane to said higher hydrocarbons.

2. A method in accordance with claim 1 wherein the solid contact material is a contact material consisting essentially of: (1) at least one Group IA metal, (2) titanium, (3) oxygen and (4) at least one material selected from the group consisting of halogen ions and compounds containing halogen ions.

3. A method in accordance with claim 2 wherein the at least one Group IA metal is a metal selected from the group consisting of lithium, sodium and potassium.

4. A method in accordance with claim 2 wherein the at least one Group IA metal is present in an amount in excess of any amount present in electrically neutral compounds of said at least one Group IA metal, said titanium and oxygen.

5. A method in accordance with claim 1 wherein the solid contact material is a contact material consisting essentially of: (1) at least one Group IIA metal, (2) titanium, (3) oxygen and (4) at least one material selected from the group consisting of halogen ions and compounds containing halogen ions.

6. A method in accordance with claim 5 wherein the at least one Group IIA metal is a metal selected from the group consisting of magnesium, calcium, strontium and barium.

7. A method in accordance with claim 5 wherein the at least one Group IIA metal is present in an amount in excess of any amount present in electrically neutral compounds of said at least one Group IIA metal, said titanium and oxygen.

8. A method in accordance with claim 1 wherein the solid contact material is a contact material consisting essentially of: (1) at least one Group IA metal, (2) at least one Group IIA metal (3) titanium, (4) oxygen and (5) at least one material selected from the group consisting of halogen ions and compounds containing halogen ions.

9. A method in accordance with claim 1 wherein the at least one Group IA metal is a metal selected from the Group consisting of lithium, sodium, and potassium.

10. A method in accordance with claim 8 wherein the Group IIA metal is a metal selected from the group consisting of magnesium, calcium, strontium and barium.

11. A method in accordance with claim 8 wherein at least one of the at least one Group IA metal and the at least one Group IIA metal is present in an amount in excess of any amount present in electrically neutral compounds of said at least one Group IA metal, said titanium and oxygen and said at least one Group IIA metal, said titanium and oxygen.

12. A method in accordance with claim 1 wherein the solid contact material is a contact material consisting essentially of: (1) at least one Group IA metal, (2) titanium and (3) oxygen.

13. A method in accordance with claim 12 wherein the at least one Group IA metal is a metal selected from the group consisting of lithium, sodium and potassium.

14. A method in accordance with claim 12 wherein the at least one Group IA metal is present in an amount in excess of any amount present in electrically neutral compounds of said at least one Group IA metal, said titanium and oxygen.

15. A method in accordance with claim 1 wherein the solid contact material is a contact material consisting essentially of: (1) at least one Group IIA metal, (2) titanium and (3) oxygen.

16. A method in accordance with claim 15 wherein the at least one Group IIA metal is a metal selected from the group consisting of magnesium, calcium, strontuim and barium.

17. A method in accordance with claim 15 wherein the at least one Group IIA metal is present in an amount in excess of any amount present in electrically neutral compounds of said at least one Group IIA metal, said titanium and oxygen.

18. A method in accordance with claim 1 wherein the solid contact material is a contact material consisting essentially of: (1) at least one Group IA metal, (2) at least one Group IIA metal, (3) titanium and (4) oxygen.

19. A method in accordance with claim 18 wherein the at least one Group IA metal is a metal selected from the Group consisting of lithium, sodium and potassium.

20. A method in accordance with claim 18 wherein the Group IIA metal is a metal selected from the group consisting of magnesium, calcium, strontium and barium.

21. A method in accordance with claim 18 wherein at least one of the Group IA metal and at least one Group IIA metal is present in an amount in excess of any amount present in electrically neutral compounds of said at least one Group IA metal, the titanium and oxygen and said at least one Group IIA metal, the said titanium and oxygen.

22. A method in accordance with claim 18 wherein the feed material gas comprising methane is natural gas.

23. A method in accordance with claim 1 wherein the volumetric ratio of methane to free oxygen is at least 1/1.

24. A method in accordance with claim 1 wherein the volumetric ratio of methane to free oxygen is between about 1/1 and about 30/1.

25. A method in accordance with claim 1 wherein the temperature of contacting is at least about 500° C.

26. A method in accordance with claim 1 wherein the temperature of contacting is between about 500° C. and about 1500° C.

* * * * *